US012781193B2

(12) United States Patent
Jin et al.

(10) Patent No.: US 12,781,193 B2
(45) Date of Patent: Nov. 3, 2026

(54) METHOD FOR PREPARING TUMOR-DERIVED MICROPARTICLES BY MICROWAVE

(71) Applicant: Union Hospital, Tongji Medical College, Huazhong University of Science and Technology, Wuhan (CN)

(72) Inventors: Yang Jin, Wuhan (CN); WenJuan Chen, Wuhan (CN); MengFei Guo, Wuhan (CN); JingJing Deng, Wuhan (CN); YaLi Wu, Wuhan (CN)

(73) Assignee: Union Hospital, Tongji Medical College, Huazhong University of Science and Technology, Wuhan (CN)

( * ) Notice: Subject to any disclaimer, the term of this patent is extended or adjusted under 35 U.S.C. 154(b) by 682 days.

(21) Appl. No.: 18/331,956

(22) Filed: Jun. 9, 2023

(65) Prior Publication Data

US 2024/0141301 A1 May 2, 2024

Related U.S. Application Data

(63) Continuation of application No. PCT/CN2023/088119, filed on Apr. 13, 2023.

(30) Foreign Application Priority Data

Nov. 2, 2022 (CN) ......................... 202211364814.4

(51) Int. Cl.
*C12N 5/09* (2010.01)
*C12N 13/00* (2006.01)

(52) U.S. Cl.
CPC ........... *C12N 5/0693* (2013.01); *C12N 13/00* (2013.01)

(58) Field of Classification Search
CPC .... C12N 5/0693; C12N 13/00; C12N 5/0012; C12N 2529/00
See application file for complete search history.

(56) References Cited

PUBLICATIONS

Liu, G.H., Chen, T., Zhang, X., Ma, X.L. and Shi, H.S., 2022. Small molecule inhibitors targeting the cancers. MedComm, 3(4), p. e181. (Year: 2022).*

Li, Z., Yu, L., Chen, D., Meng, Z., Chen, W. and Huang, W., 2020. Protocol for generation of lung adenocarcinoma organoids from clinical samples. Star Protoc. 2, 100239 [online] (Year: 2020).*

Ma, J., Zhang, H., Tang, K. and Huang, B., 2020. Tumor-derived microparticles in tumor immunology and immunotherapy. European Journal of Immunology, 50(11), pp. 1653-1662. (Year: 2020).*

Zhang Huafeng, "The Effect of Tumor Cell-Derived Microparticles on Tumor Growth, Metastasis and Their Mechanism", China Doctoral Dissertations Full-Text Database, Medical Health Science and Technology, Jan. 15, 2017, E072-5.

Song Xiaaolian, "The Effect of Microwave Irradiation on Apoptosis of Lung Cancer A549 Cells", China Master's Theses Full-Text Database, Medical Health Science and Technology, Sep. 15, 2006, E072-70.

* cited by examiner

*Primary Examiner* — Jeremy C Flinders
*Assistant Examiner* — Masudur Rahman

(57) ABSTRACT

A method for preparing a tumor-derived microparticle by a microwave includes the following steps: step 1, Lewis lung carcinoma (LLC) of a lung adenocarcinoma cell line is taken and then the LCC is cultured in a culture dish for more than 24 hours (h) to obtain cultured cells; step 2, microwave heating treatment is performed on the cultured cells obtained in step 1 to obtain treated cells; step 3, the treated cells obtained in step 2 are placed into a constant temperature incubator for cultivation for 24 h; and step 4, a supernatant of cells is collected from the culture dish cultured in step 3, and multiple centrifugation treatments is performed on the supernatant by using a density gradient centrifugation method to obtain a precipitate which is the tumor-derived microparticle $TMP_{MW}$.

4 Claims, 14 Drawing Sheets

METHOD FOR PREPARING TUMOR-DERIVED MICROPARTICLES BY MICROWAVE

CROSS-REFERENCE TO RELATED APPLICATION

The application claims priority to Chinese patent application No. 202211364814.4, filed on Nov. 2, 2022, and titled with "METHOD FOR PREPARING TUMOR-DERIVED MICROPARTICLES BY MICROWAVE", and the entire contents of the above-mentioned application are hereby incorporated herein by reference.

TECHNICAL FIELD

The disclosure relates to a field of a therapeutic drug technology for tumor inhibitors, in particular to a method for preparing a tumor-derived microparticle by a microwave.

BACKGROUND

For decades, extracellular vesicles (EVs) have attracted a great attention in various research fields and are rapidly developing. All cell types from bacteria to mammals can secrete the EVs, which is a highly conserved physiological process. The secreted EVs are nanoscale particles coated by cell membranes and loaded with various active molecular substances from cells, playing an important role in intercellular interactions and regulating the physiological process and a pathological process. The EVs are mainly divided into two categories: extracellular vesicles and microparticles (MPs, also known as microbubbles). The extracellular vesicle has a size of approximately 40-150 nanometers (nm), while the MP has a diameter range between 150 nm and 1000 nm, therefore the extracellular vesicles and the MPs are referred to as small EVs and large EVs, respectively.

At present, mechanisms of tumor-derived MPs (TMPs) in a tumor development, invasion and metastasis, and an induction of a drug resistance have been widely studied. For example, a tumor cell enhances a communication with one of a tumor and a stromal cell through a paracrine secretion, thus accelerating a tumor growth and promoting a metastasis, and also mediating a generation of an immunosuppressive tumor microenvironment (TME). In addition, because the TMPs have a bilayer phospholipid membrane structure and carry a biological active substance of the cell itself, the TMPs have strong and flexible plasticity and drug encapsulating ability (the drug is any one of a small molecule compound, a lipid, a protein, and a nucleic acid, etc.). At present, a large number of research teams and biological companies are developing and adopting different production, synthesis, and modification technologies to continuously innovate and improve, and are committed to transforming the TMPs into an effective means of treating the tumor.

The TMPs often originate from human or mouse derived tumor cell lines. In addition, researchers have extracted the TMPs from patient tumor tissues for a development of an innovative tumor treatment strategy. It is worth mentioning that various processing, separation, and purification processes are constantly emerging to obtain the TMPs. The most important core step in extracting the TMPs is a centrifugation, including a gradient centrifugation and/or a high-speed centrifugation. However, for different research purposes and technical levels, there are often unique and different treatment strategies before and after the centrifugation to obtain the TMPs, in order to change a biological function of the TMPs and achieve a goal of treating the tumor. Current methods for preparing the TMPs mainly include five methods.

(1) A tumor cell in good condition naturally secretes the TMPs. In theory and practice, it is found that the naturally secreted TMPs have a tumor promoting effect. Therefore, for the TMPs, the researchers choose to give the cell one of micro ribonucleic acid (miRNA) transfection and small interfering ribonucleic acid (siRNA) transfection and other modification treatments during the natural secretion, or secrete and extract the TMPs, and then load goods through a chemical bond coupling or one of a physical perforation and a physical adsorption and other methods, thereby endow the TMPs with inhibition or killing of the tumor cell and enhance an efficacy.

(2) The tumor cell is subjected to an ultraviolet (UV) irradiation and then the TMPs are extracted. Before separating the TMPs, an appropriate cell culture time should be reserved to allow tumor cells with UV induced nuclear damage to secrete a large amount of the TMPs. Previous research found that the TMPs prepared based on the UV irradiation have a certain cytotoxicity in vitro, but have no significant anti-tumor effect in an animal model. Therefore, an additional modification is needed to obtain one of an ability to control the tumor growth and the ability to inhibit the tumor growth. For example, the TMPs encapsulating a methotrexate are used to treat patients with an advanced lung cancer and a malignant pleural effusion, and results suggest that the TMPs have a certain therapeutic value.

(3) The tumor cell secretes the TMPs after a radiation stimulation. Some of the researchers have found that the TMPs extracted from radiotherapy cells inhibit a cancer cell growth at a cellular level and an animal level through pathways such as inducing immunogenic death. Meanwhile, compared to the TMPs produced after the UV induction, the TMPs extracted from the radiotherapy cells have the stronger cytotoxicity.

(4) The tumor cell secretes the TMPs under a stress state after a drug treatment. When the cells are stimulated by the drug (such as a tyrosine kinase inhibitor) and are in the stress state, one of an apoptosis and the death occurs. During the process, the tumor cell is more likely to secrete vesicles with the membrane structures, and the contents of vesicles are significantly different from the natural TMPs. For example, an increase in tumor antigen components enhances an immunogenicity of the TMPs and induces specific anti-tumor immune responses.

(5) One of the uniform TMPs and the specific TMPs is obtained through purification. The TMPs obtained after the high-speed centrifugation are often doped with impurities such as a smaller fragment, an exosome, a larger apoptotic body, and aggregated MPs, etc. Therefore, the researchers use a method such as any one of a size exclusion, three-dimension (3D) culture of the EVs and etc. to maximizes a uniformity and a yield of the TMPs after one of a uniform pore filtration and a spherical culture separation. In addition, modified labeled adsorption beads and specific targeted binding TMPs, are eluted and purified to obtain the target TMPs, further improving the purity of the preparation.

Drawbacks of existing methods for preparing the TMPs are as follows.

(1) A production and preparation process of the TMPs is complex. Many existing studies have conducted complex and diverse modifications on the TMPs to enhance the tumor efficacy, but meanwhile, a complexity of the preparation process is increased, resulting in an increased cost consumption. An ultimate goal of preparing the TMPs is to apply the TMPs to clinical tumor patients, which ultimately leads to a production efficiency and cost issues in a clinical transformation, such as prolonged treatment cycles for the patients.

(2) The TMPs have a low production capacity and a long production time. Although the cells continue to secrete the EVs, a secretion quantity of the cells is not balanced with treatment needs. In practice, a large number of the TMPs need to be collected to meet the treatment needs at one of a preclinical animal level and a clinical patient level. Meanwhile, in order to produce the sufficient TMPs, a significant amount of the production time is required.

(3) A preparation cost is high and a clinical burden is heavy. Due to the complex preparation process of the therapeutic TMPs and expensive additional modifications carried out by the researchers, (the additional modification is such as a genetic engineering technique, a encapsulating monoclonal antibody, and an individualized tumor new antigen peptide, etc.) a significant amount of the costs and capital consumptions is incurred. Then, in a process of the clinical transformation therapy for the tumor, it potentially increases an economic burden on the patients.

(4) Biosafety is questionable and clinical applications are limited. In addition to problems faced in the clinical transformation, there is a major challenge that the biological safety of TMPs generated based on current technology cannot be confirmed. For example, during an activation of the immune responses, the TMPs may activate a complement system, resulting in mild to severe allergic adverse reactions. In addition, a large number of the TMPs edited by genetic engineering carry the siRNA, the miRNA, a deoxyribonucleic acid (DNA) plasmid and other nucleic acid substances, which causes deep thinking in medical ethics, such as whether the TMPs edited by genome editing cause somatic mutation of the patients, or whether the TMPs affect a heredity of the patients.

(5) The efficacy of the TMPs in the tumor treatment is uncertain. Although the single natural TMPs activate the immune responses in vivo, because the TMPs contain a lot of biological information of their own cells (such as a tumor antigen peptide, a nucleic acid, etc.), the TMPs are born with the ability to help the tumor cell escape from immune surveillance or promote the generation of tumor immune suppression microenvironment. Therefore, the researchers are transforming the TMPs and focusing on the research of a tumor vaccine, but most of the researchers remain at a preclinical level to explore the efficacy of the tumor vaccine, and a clinical efficacy of tumor vaccine is still unpredictable.

SUMMARY

A technical problem to be solved in the disclosure is to provide a method for preparing a tumor-derived microparticle by a microwave in response to issues and requirements mentioned above.

To solve the technical problem, following technical solutions are adopted in the disclosure.

A method for preparing a tumor-derived microparticle by a microwave includes following steps:

step 1, Lewis lung carcinoma (LLC) of a lung adenocarcinoma cell line is taken and then the LCC is cultured in a culture dish for more than 24 hours (h) to obtain cultured cells;

step 2, microwave heating treatment is performed on the cultured cells obtained in step 1, with a microwave power of 350-700 watts (W) and a heating time of 10-20 seconds (s) to obtain treated cells;

step 3, the treated cells obtained in step 2 is placed into a constant temperature incubator for cultivation for 24 h; and step 4, a supernatant of cells is collected from the culture dish cultured in step 3, and multiple centrifugation treatments are performed on the supernatant by using a density gradient centrifugation method to obtain a precipitate which is the tumor-derived microparticle $TMP_{MW}$.

In an embodiment, in step 2, a microwave power is 700 W and a heating time is 20 s.

In an embodiment, in step 3, a cultivation temperature of the constant temperature incubator is 37° C. and a concentration of $CO_2$ is 5%.

The tumor microparticle prepared by the above method.

An application of the tumor microparticle includes: preparing one of a tumor inhibitor and a therapeutic drug by using the tumor-derived microparticle.

An application of the tumor microparticle includes: using the tumor-derived microparticle as a therapeutic drug encapsulating platform material.

After adopting the technical solutions, the disclosure has following seven advantages compared to the related art.

(1) A device of the disclosure is easy to obtain, a technology of the disclosure is simple, and the preparation process of the disclosure is simple. At present, a microwave device is easy to obtain in a laboratory, and a preparation of the TMPs using a microwave technology greatly simplifies the preparation process due to its low requirements for a high technology.

(2) Time and economic costs of the disclosure are saved. Due to the simple preparation process and low device prices, the time and cost of preparing the TMPs are greatly reduced.

(3) The production of microparticles (MPs) of the disclosure is considerable. Based on the preparation of the TMPs by microwave, the amount of the TMPs secreted, separated and extracted by cells is large, which improves the yield and extraction efficiency.

(4) Biosafety of the disclosure is improved. The TMPs prepared by the microwave have no cytotoxicity in vitro and no significant toxic side effects in animal models.

(5) Some of original properties and functions of the TMPs of the disclosure are retained. Although the cells are subjected to a microwave heating treatment before collecting the TMPs by centrifugation, they still carried the bioactive molecules of the original cells, retaining the biological functions of cell microparticles such as biocompatibility, targeting, and intercellular communication.

(6) A tumor microenvironment of the disclosure is regulated and a tumor growth of the disclosure is inhibited. The TMPs prepared by the microwave contain tumor antigens, and the $TMP_{MW}$ are found at an animal level to stimulate an anti-tumor immune response and have a potential to become tumor vaccines, thereby inhibiting the tumor growth.

(7) The disclosure provides a novel nano particle drug encapsulating platform. The TMPs prepared by the microwave not only have the potential to regulate a tumor immune microenvironment, but also are used as the novel drug encapsulating platform for extracellular vesicles. Taking advantage of the characteristics of a flexibility, a variability and a stability of a cell membrane of the TMPs, the drug for a tumor treatment is loaded and targeted to a tumor tissue to improve the efficacy of a single drug.

BRIEF DESCRIPTION OF DRAWINGS

In order to provide a clearer explanation of technical solutions in embodiments, a brief introduction is given to accompanying drawings required in a description of the embodiments. It is evident that the accompanying drawings in the following description are some of the embodiments of the disclosure. For those skilled in the art, other accompanying drawings can be obtained based on the drawings in the following description without creative efforts.

DETAILED DESCRIPTION OF EMBODIMENTS

The disclosure provides a clear and a complete description of technical solution in following embodiments in conjunction with accompanying drawings. Obviously, following embodiments are only a part of embodiments, not all of the embodiments. Based on the embodiments in the disclosure, all other embodiments obtained by those skilled in the art without creative labor fall within a scope of a protection in the disclosure.

1. Effects of a Microwave on a Cell Growth and a Cell Morphology

Figure 1:
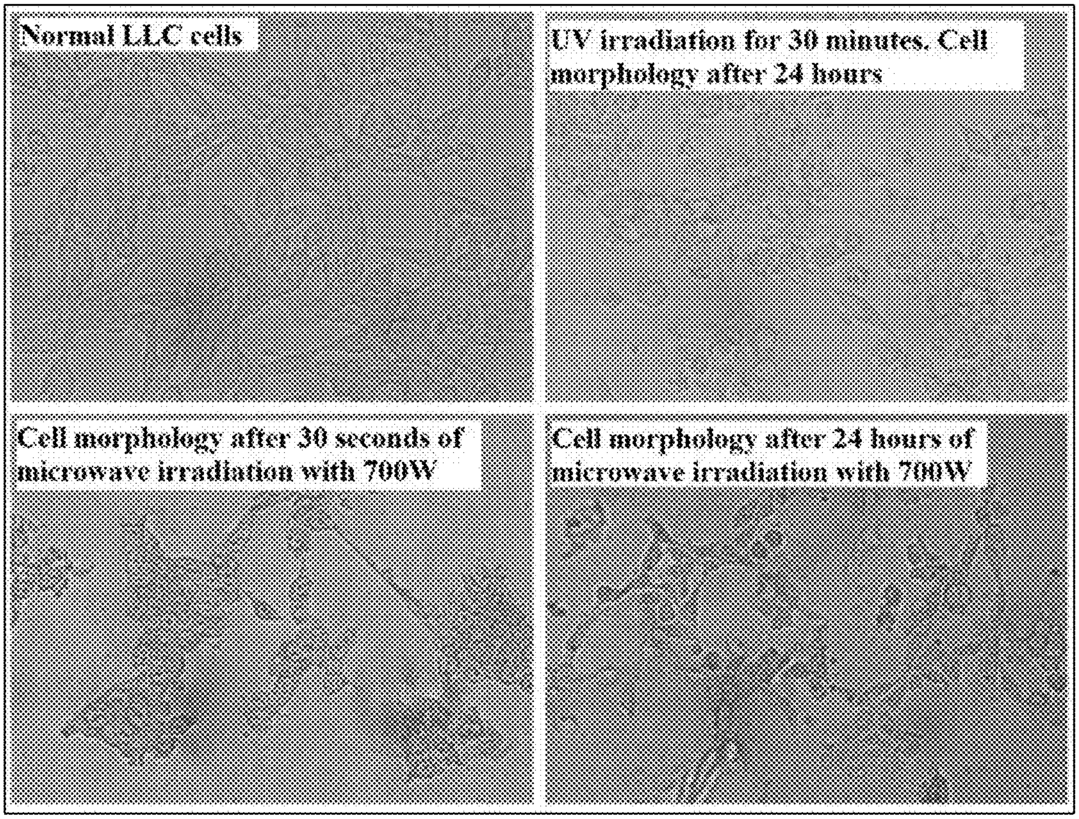
FIG. 1 is a schematic diagram of a morphology of a cancer cell under a 40× optical microscope.

After a cell is subjected to a microwave radiation with an output power of 700 W, the cell continues to be cultured in an incubator (a culturing temperature is 37° C. and a $CO_2$ concentration is 5%). Morphological changes of the cell after the microwave irradiation at 30 seconds (s) and 24 hours (h) are observed, respectively (FIG. 1). Compared to a normal Lewis lung carcinoma (LLC) cell, after 30 s of the microwave irradiation, a cell membrane is intact, a nucleus appears pyknotic in a shape of fine black dot, and a cell density is decreased. However, after 24 h, the difference in a cell morphology is greater, and an integrity of the cell membrane is further disrupted, resulting in a decrease in the cell density. Previously, the TMPs were extracted through an ultraviolet (UV) irradiation induction. As shown in FIG. 1, after 24 h of a cell culture under the UV irradiation, there are significant differences in the cell morphology, such as a cell fragmentation and a cell growth inhibition, which are somewhat different from the morphological changes of cancer cells under a microwave stimulation. Based on a theory that more tumor-derived microparticles (TMPs) are released during a process of cell apoptosis and cell death, a preparation and an extraction of the TMPs using a microwave technology will be carried out as follows.

2. A Preparation of a Microwave-Mediated Tumor-Derived Microparticle ($TMP_{MW}$)

2.1 An Exploration and a Determination of Microwave Conditions

About $1\times10^8$ LLC cells of the lung adenocarcinoma cell line are stably grown on a wall in a culture dish for 24 h, then the culture dish is placed on a heating tray of a microwave device (a working frequency is 240 megahertz (MHz), a maximum output function rate is 700 watts (W)), the following microwave conditions of the microwave device are chosen: (1) a microwave output frequency is 175 W, a heating time is 10 s; (2) a microwave output frequency is 175 W, a heating time is 20 s; (3) a microwave output frequency is 350 W, a heating time is 10 s; (4) a microwave output frequency is 350 W, a heating time is 20 s; (5) a microwave output frequency is 700 W, a heating time is 10 s; and (6) a microwave output frequency is 700 W, a heating time is 20 s. For experimental safety reasons, a maximum heating setting time is 20 s.

According to the above 6 microwave conditions, the cells are heated and the culture dish is placed in a constant temperature incubator (a cultivation temperature is 37° C., a $CO_2$ concentration is 5%) for 24 h. After 24 h, a first supernatant about 45 milliliters (ml) is collected from the culture dish and put in a 50 ml centrifuge tube, and the TMPs are extracted based on a previous gradient centrifugation technology. Specifically, Firstly, the first supernatant in the 50 ml centrifuge tube is subjected to centrifugation at a relative centrifuge force of 200×g (a unit for g is gravitational acceleration, i.e., 9.8 meters per square second (m/s 2)) for 10 minutes (min), then a cell precipitate is discarded and a second supernatant is retained for a further centrifugation. The second supernatant is subjected to centrifugation at a relative centrifuge force of 2000×g for 30 min to obtain impurities such as cell fragments and a third supernatant. The impurities are discarded and the third supernatant is collected into a new sterile centrifuge tube. Finally, the third supernatant is subjected to centrifugation at a relative centrifuge force of 18000×g for 60 min to obtain a fourth supernatant and a precipitate. After the centrifugation, the precipitate obtained by discarding the fourth supernatant is the $TMP_{MW}$. The $TMP_{MW}$ is washed once with 1 ml sterile phosphate buffer solution (PBS), and the centrifugation conditions for the cleaning are at a relative centrifuge force of 18000×g for 60 min. After the cleaning, about 100 microliters (ul) of the PBS are added to the $TMP_{MW}$, then the $TMP_{MW}$ are gently blew and mixed, and the $TMP_{MW}$ are stored in a refrigerator at −80° C.

Figure 2:
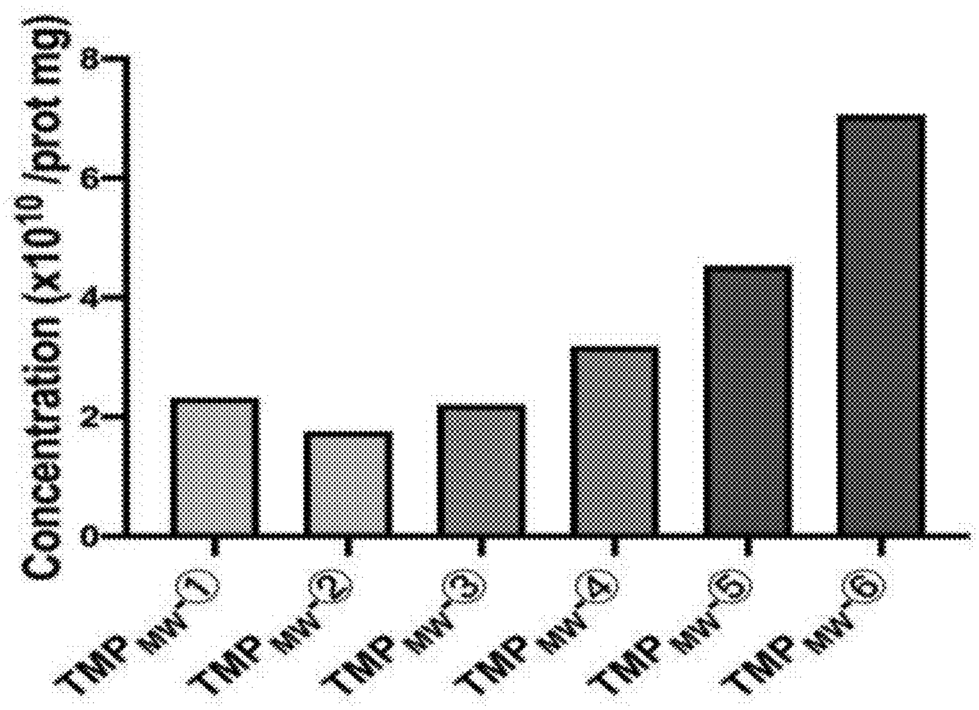
FIG. 2 is a schematic diagram of a comparison of $TMP_{MW}$ yields under different microwave conditions.
Figure 3:
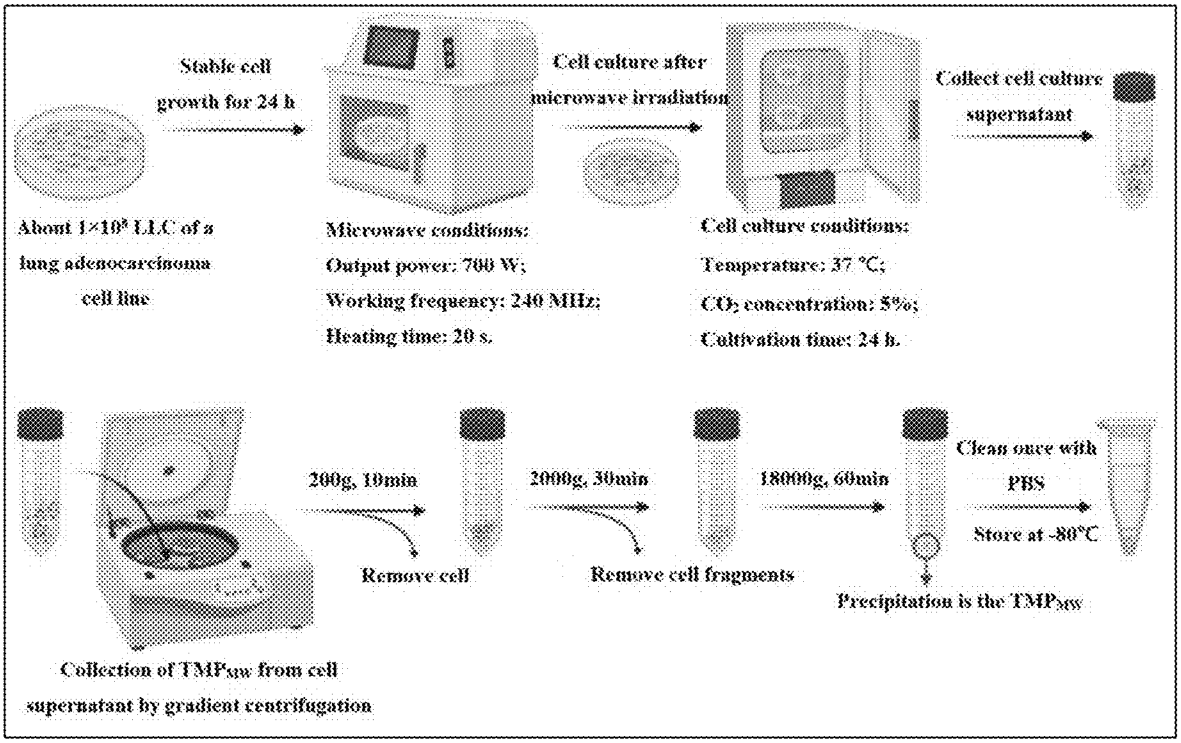
FIG. 3 is a flowchart of a preparation method in the disclosure.

Based on the 6 microwave conditions mentioned, the $TMP_{MW}$ prepared under different conditions are collected. Next, in order to determine whether there is a yield difference, a content determination is carried out. Firstly, a protein concentration of the $TMP_{MW}$ is determined using a protein concentration assay (i.e., bicinchoninic acid (BCA) test). Afterwards, a nanoparticle tracking system (NTA) experiment is conducted to detect a number of the $TMP_{MW}$ in a sample. Then, by standardizing the NTA results with the protein concentration, whether there is the best yield under the different microwave conditions is determined. From statistical results in FIG. 2, it is seen that under the microwave output frequency of 700 W and the heating time of 20 s, the highest yield of the $TMP_{MW}$ is achieved. Therefore, in subsequent experiments, the $TMP_{MW}$ is prepared using this microwave condition (see FIG. 3 for a preparation process).

2.2 The Yield of $TMP_{MW}$ is Higher than that of $TMP_{UV}$

Figure 4A:
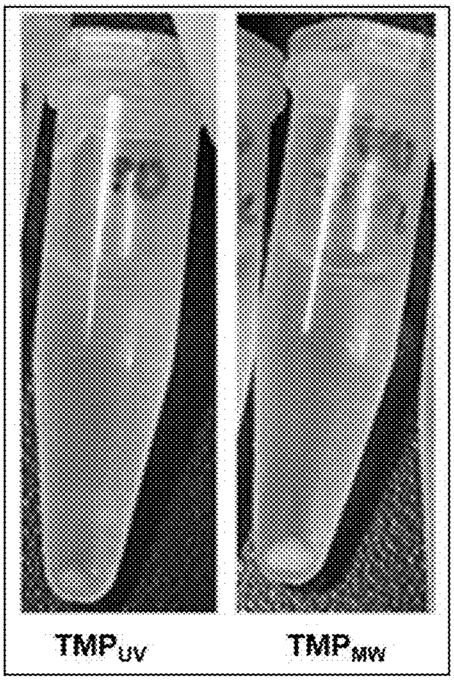
FIG. 4A is a schematic diagram of an actual yield comparison of the $TMP_{MW}$ and a $TMP_{UV}$.
Figure 4B:
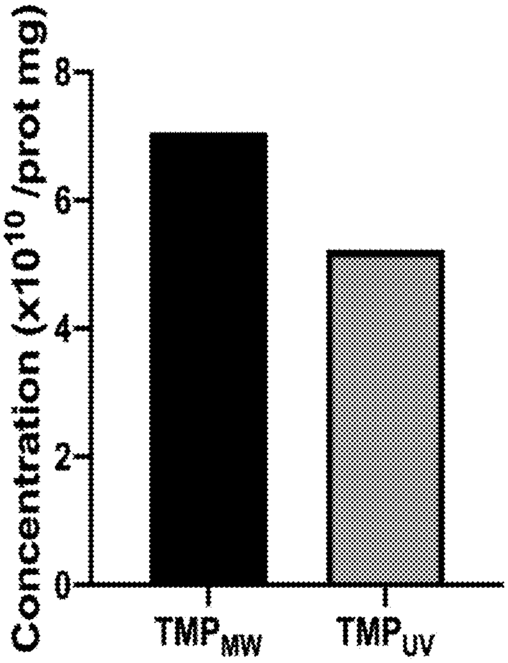
FIG. 4B is a schematic diagram of a concentration comparison of the $TMP_{MW}$ and the $TMP_{UV}$.

In addition, the yield of the $TMP_{MW}$ with that of the yield of the $TMP_{UV}$ induced by the UV radiation are compared. The precipitate obtained by PBS cleaning and centrifugation (a white precipitate at a bottom of the centrifuge tube is the $TMP_{MW}$) intuitively shows that the yield of the $TMP_{MW}$ is higher than the yield of the $TMP_{UV}$ (FIG. 4A). In addition, the BCA test and the NTA experiment are used to detect the protein concentration and particle numbers in the samples, and after a calculation and a comparison, it is found that the yield of the $TMP_{MW}$ is higher (FIG. 4B).

3. Identifying the $TMP_{MW}$ 3.1 A Size and a Concentration of the $TMP_{MW}$

Figure 5A:
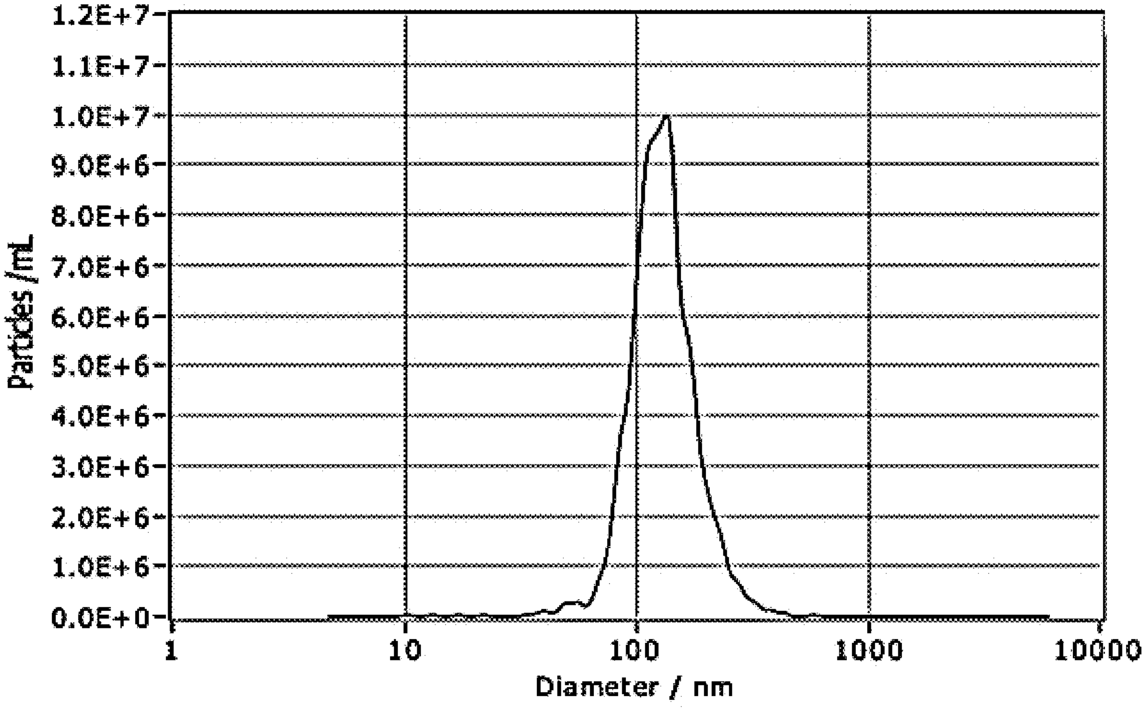
FIG. 5A is a schematic diagram of a size distribution of a TMP-F.
Figure 5B:
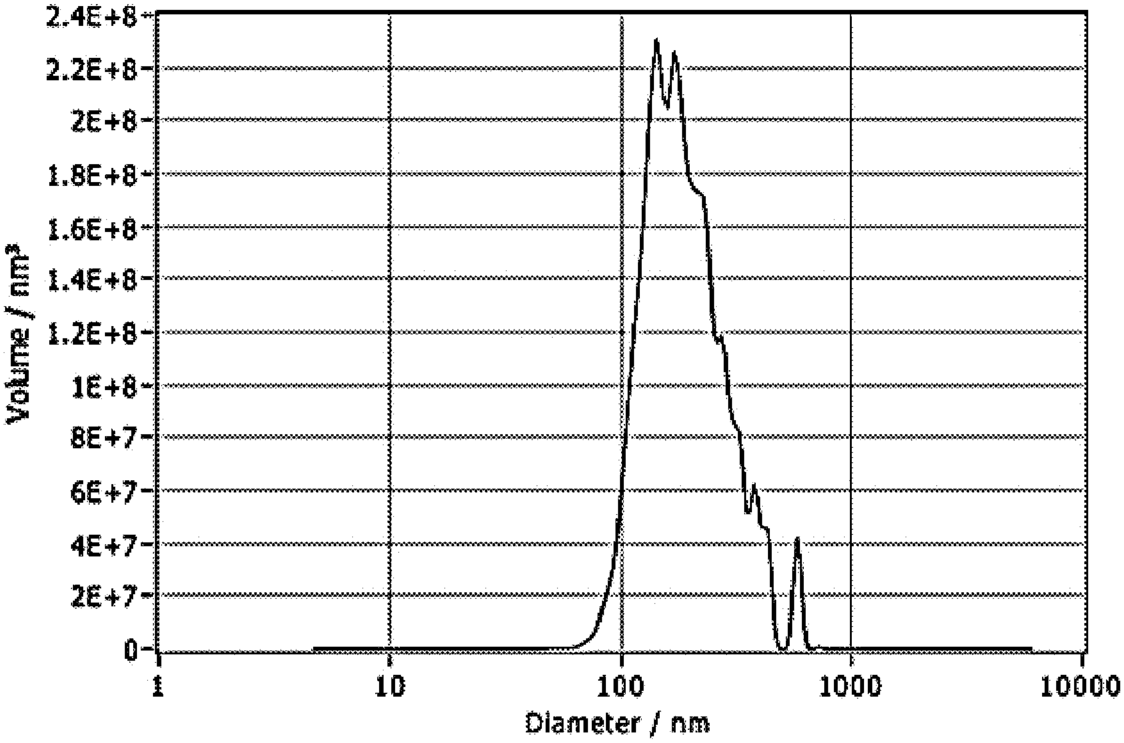
FIG. 5B is a schematic diagram of a particle concentration of the TMP-F.

The $TMP_{MW}$ is extracted under a microwave power at 700 W and a heating time for 20 s, and the size and the concentration of extracellular particles are identified through the NTA experiment. An average particle size of the $TMP_{MW}$ is 136.3 nm, with a concentration of 1.92×1012 particles per milliliter (particles/ml) (FIGS. 5A and 5B).

3.2 A Form of the $TMP_{MW}$

Figure 6:
FIG. 6 is a schematic diagram of a transmission electron microscopy (TEM) image of the prepared $TMP_{MW}$.

The extracted $TMP_{MW}$ is identified by a transmission electron microscopy (TEM) to determine a shape of the TMPs. The shape of the $TMP_{MW}$ is circular (FIG. 6).

3.3 A Membrane Marking of the $TMP_{MW}$

Figure 7:
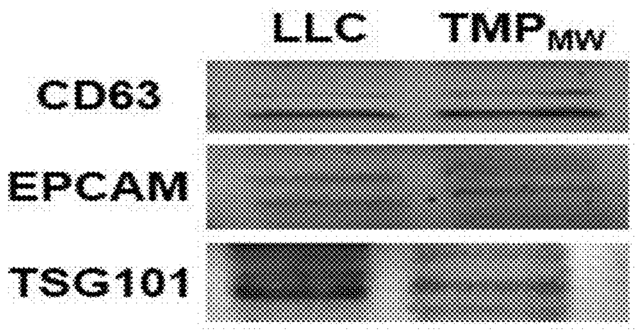
FIG. 7 is a schematic diagram of expression results of a Lewis lung carcinoma (LLC) tumor cell and a secreted $TMP_{MW}$ membrane marking of the LLC tumor cell.

An epithelial cell adhesion molecule (EPCAM), a tumor susceptibility gene 101 protein (TSG101), and a CD63 are classic TMPs marking proteins. A western blot (WB) experiment suggests that the $TMP_{MW}$ expresses the above TMPs marking proteins and successfully extracts the TMPs (FIG. 7).

Figure 8:
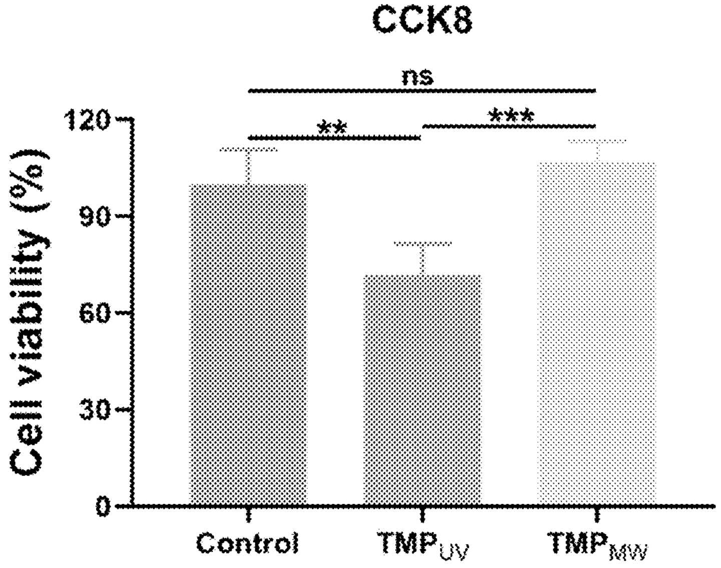
FIG. 8 is a schematic diagram of cell proliferations of the LLC after 24 hours (h) of the microparticle stimulation by an ultraviolet (UV) induced ($TMP_{UV}$) and a microwave mediated ($TMP_{MW}$); ns: no statistical significance, $P<0.01$, and *$P<0.001$.
Figure 9A:
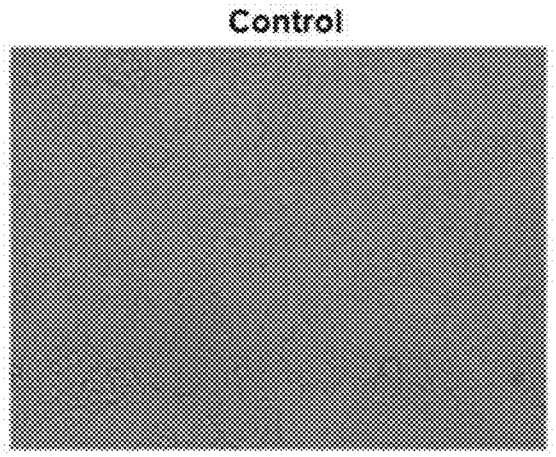
FIG. 9A is a schematic diagram of a morphology of the LLC cell in an unstimulated control group under a 20× optical microscope.
Figure 9B:
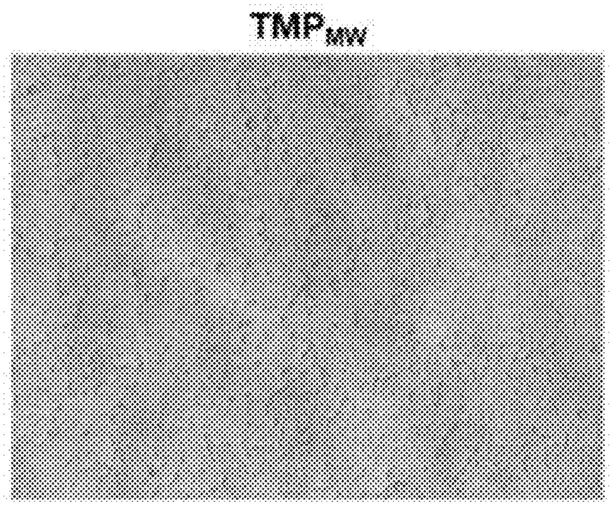
FIG. 9B is a schematic diagram of a morphology of the LLC cell in a $TMP_{MW}$ stimulated group under the 20× optical microscope.

4. The Effect of the $TMP_{MW}$ on a Cancer Cell Proliferation at a Cellular Level To explore the effect of the $TMP_{MW}$ on a lung adenocarcinoma, experiments are first conducted at the cellular level. Results of a cell proliferation experiment (i.e., a CCK8 assay) suggest that the $TMP_{MW}$ has no inhibitory effect on the cell proliferation (FIG. 8). Meanwhile, under an optical microscope, a cell state of the LLC of a lung adenocarcinoma cell line is observed 24 h after the stimulation of the $TMP_{MW}$. It is found that compared with a control group (where the cell is not subjected to an additional stimulation), the $TMP_{MW}$ did not significantly change the cell growth morphology (FIGS. 9A and 9B). The above experiments demonstrate that the $TMP_{MW}$ has no cytotoxicity.

Figure 10A:
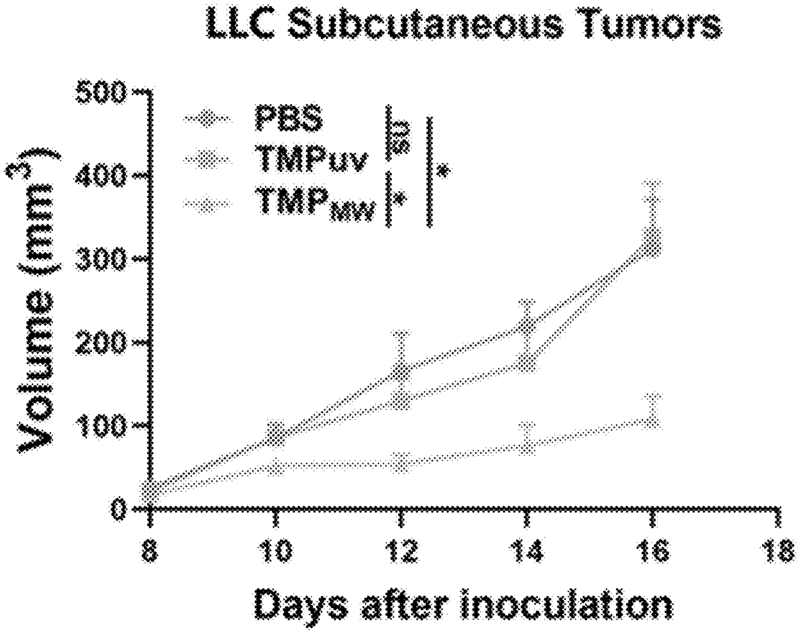
FIG. 10A is a schematic diagram of volume change curves of subcutaneous tumors in mice; ns: no statistical significance; and *$P<0.05$.
Figure 10B:
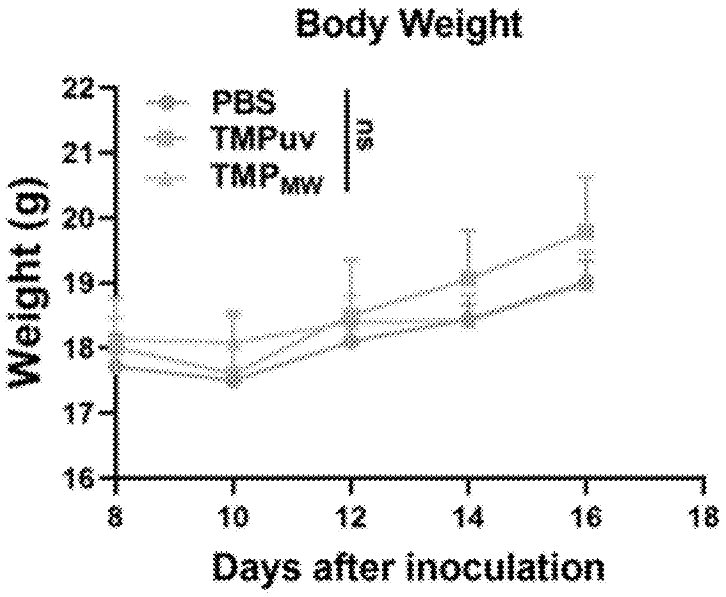
FIG. 10B is a schematic diagram of body weight changes of the mice; ns: no statistical significance; and *$P<0.05$.
Figure 11:
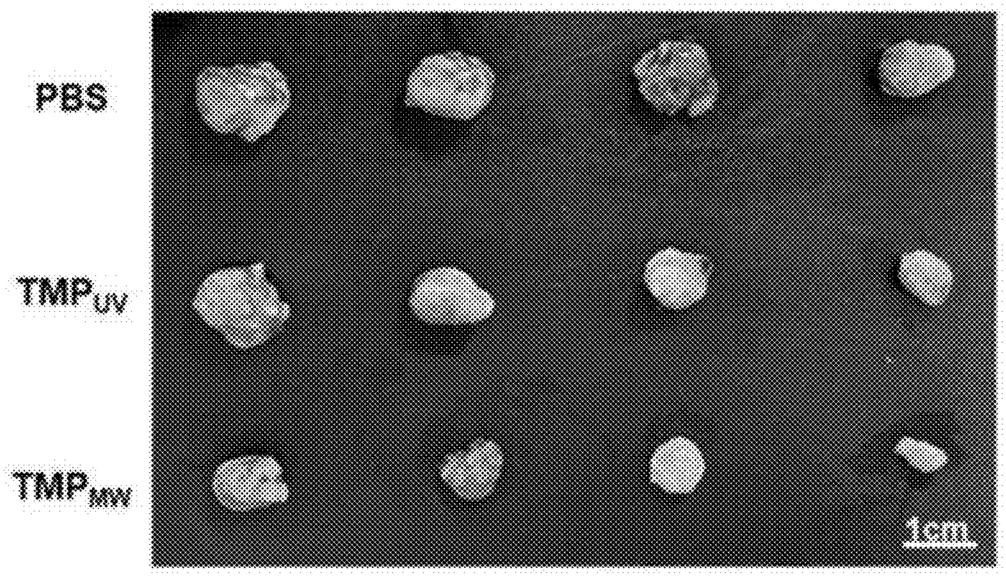
FIG. 11 is a schematic diagram of a display of nude tumors in the mice.
Figure 12A:
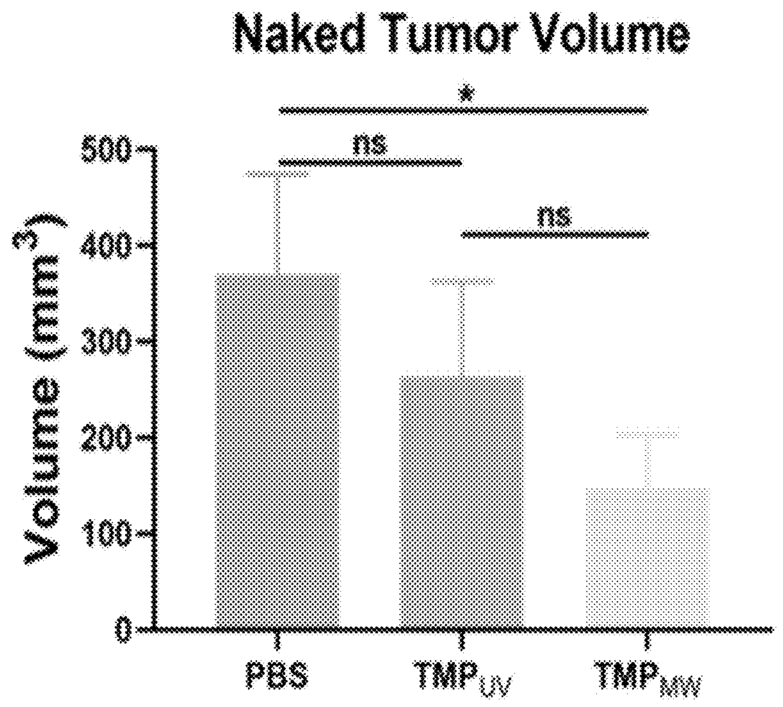
FIG. 12A is a schematic diagram of a volume map of the nude tumors in the mice; ns: no statistical significance, *$P<0.05$, and ***$P<0.001$.
Figure 12B:
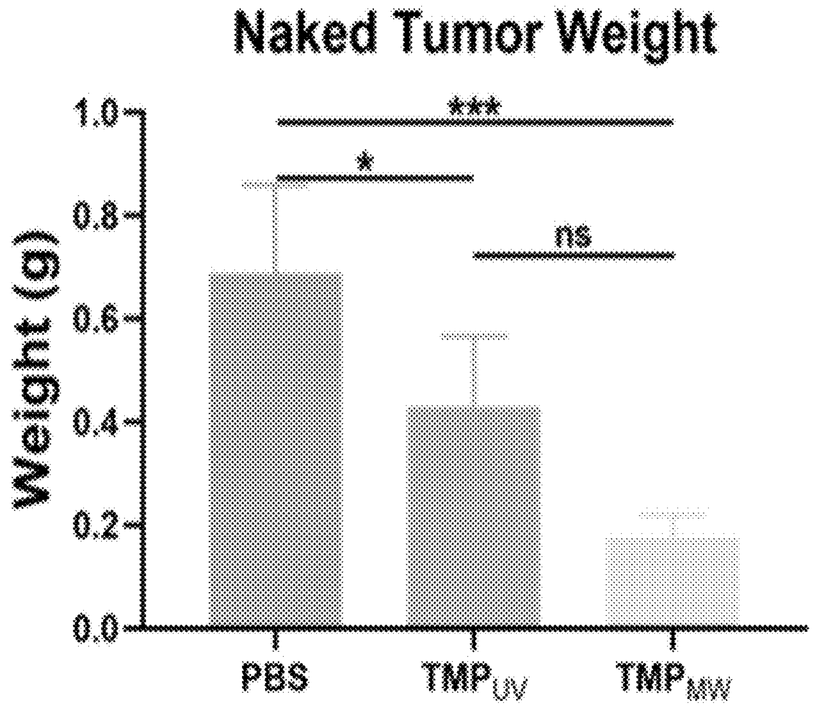
FIG. 12B is a schematic diagram of net weight statistics; ns: no statistical significance, *$P<0.05$, and ***$P<0.001$.

5. The Effect of the $TMP_{MW}$ on Tumor Bearing Mice at an Animal Level 5.1 Inhibiting a Tumor Growth At the animal level, lung adenocarcinoma (the LLC cell line) subcutaneous tumors are inoculated on right shoulder backs of C57BL/6 mice. After a growth volume of the subcutaneous tumor reaches 50 cubic millimeters (mm 3), an intervention is begun. The mice are randomly divided into 4 groups, with 4 mice in each the group. The results show that compared to the PBS group, the $TMP_{MW}$ has a significant inhibitory effect on the tumor growth. In addition, although our previous research found that the $TMP_{UV}$ exhibited cytotoxic effects in vitro, in the animal level experiment, the $TMP_{UV}$ did not significantly inhibit tumor efficacy (FIG. 10A). During the 5 interventions, there is no significant weight loss in the mice, which to some extent suggests the safety of the $TMP_{MW}$ treatment (FIG. 10B). After the 5 interventions, the subcutaneous tumors obtained from a dissection are shown in FIG. 11. The volumes and weights of subcutaneous tumors are compared and it found that the $TMP_{MW}$ has a more significant anti-tumor effect in animals compared to the $TMP_{UV}$ (FIGS. 12A and 12B).

5.2 Promoting an Apoptosis of an Intratumoral Cell

Figure 13:
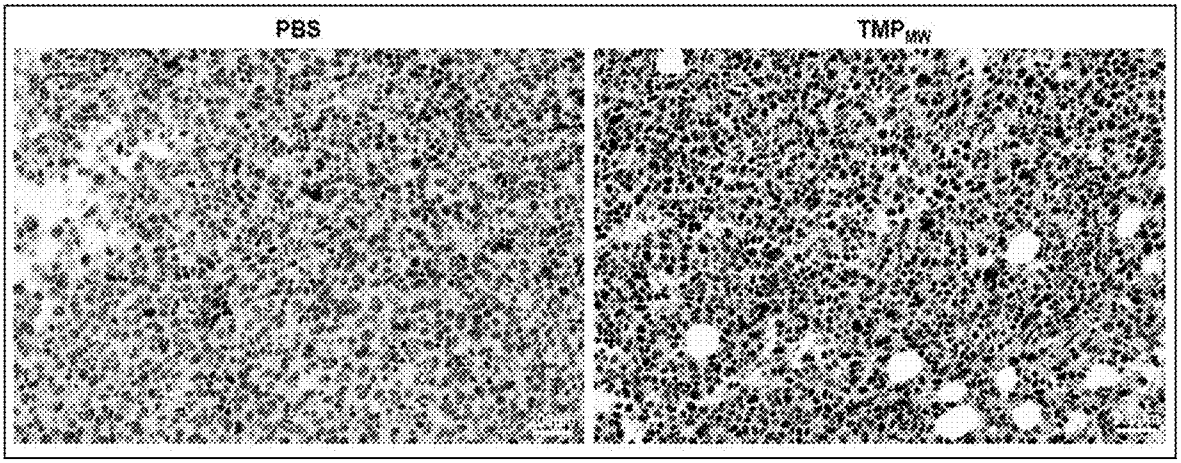
FIG. 13 is a schematic diagram of a TUNEL staining in a tumor body.
Figure 14A:
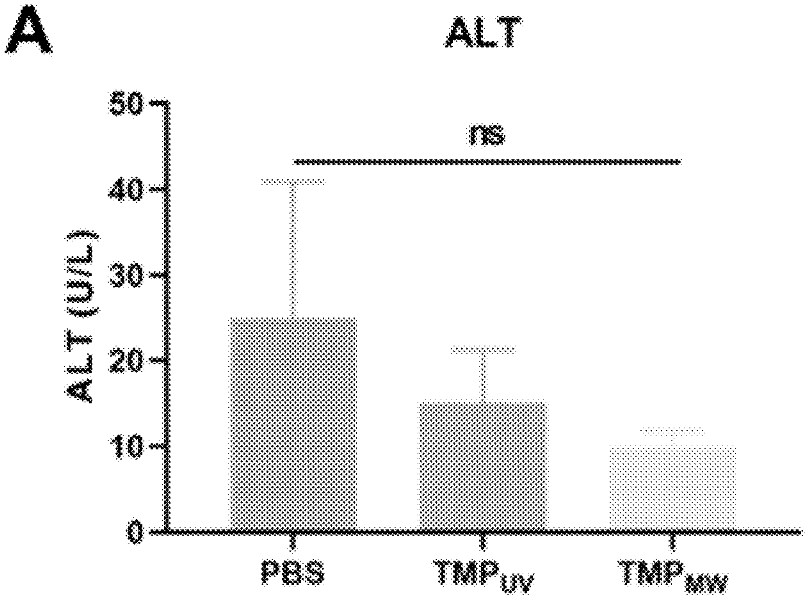
FIG. 14A is a schematic diagram of a serum at alanine transaminase (ALT) level in the mice; and ns: no statistical significance.
Figure 14B:
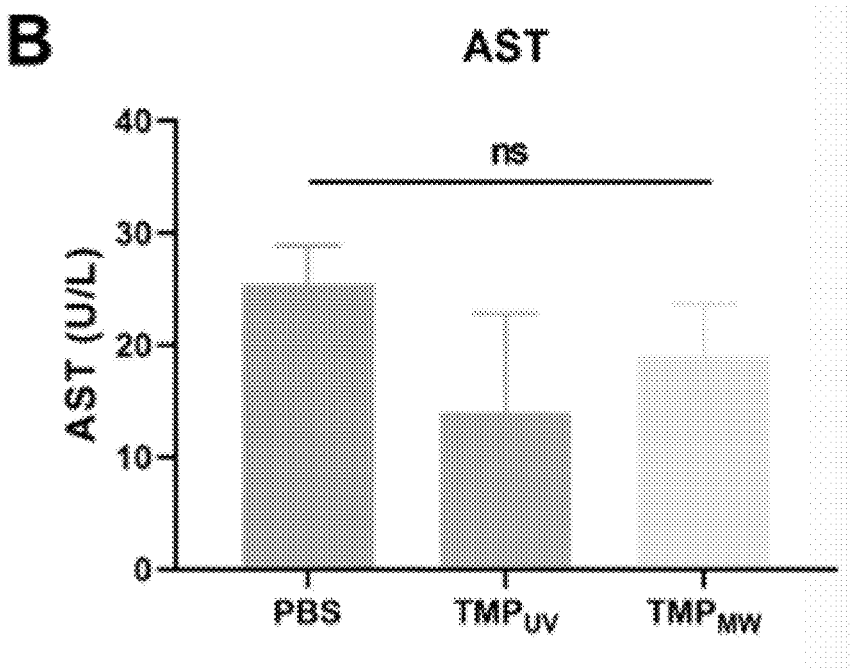
FIG. 14B is a schematic diagram of a serum at aspartate transaminase (AST) level in the mice; and ns: no statistical significance.
Figure 14C:
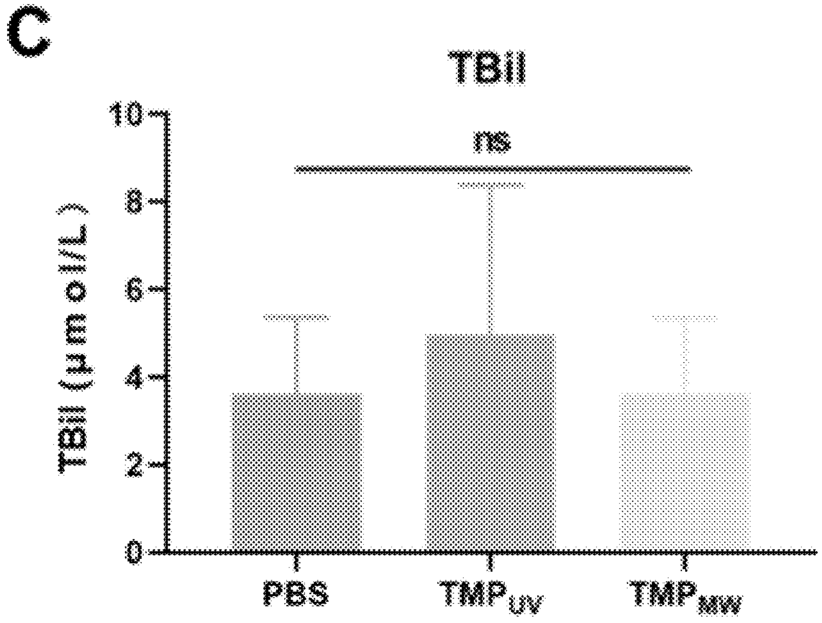
FIG. 14C is a schematic diagram of a serum total bilirubin (TBil) level in the mice; and ns: no statistical significance.
Figure 14D:
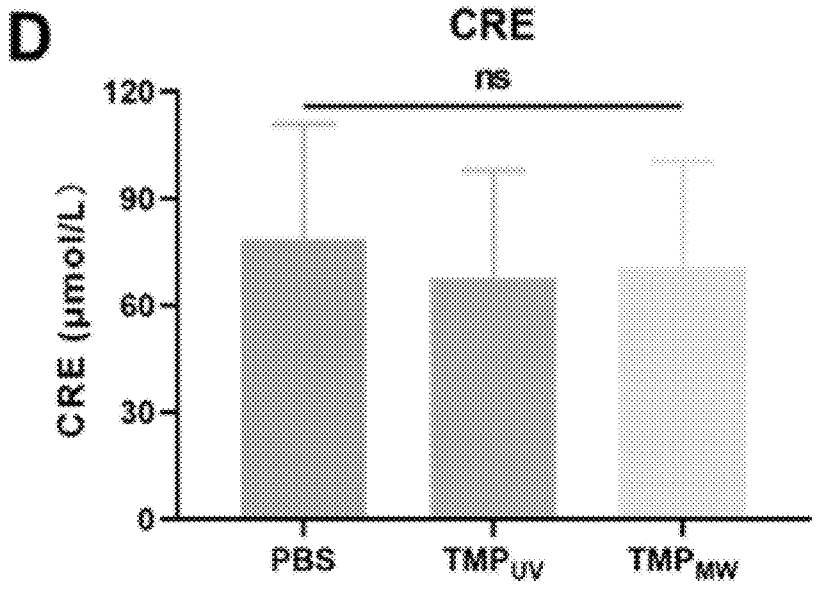
FIG. 14D is a schematic diagram of a serum at creatinine (CRE) level in the mice; and ns: no statistical significance.

A further TUNEL immunohistochemical staining of nude tumors (blue represents a nuclear staining, yellow brown represents a positive staining for apoptotic cells; and the positive staining is stronger indicating an increase in a number of the apoptotic cells). Compared to a PBS group, the number of apoptotic cells in tumor tissue significantly increased after the $TMP_{MW}$ treatment, indicating once again that the $TMP_{MW}$ has an inhibitory effect on the tumors and exerts a tumor efficacy (FIG. 13).

5.3 Verifying a Biosafety of the $TMP_{MW}$

Figure 15:
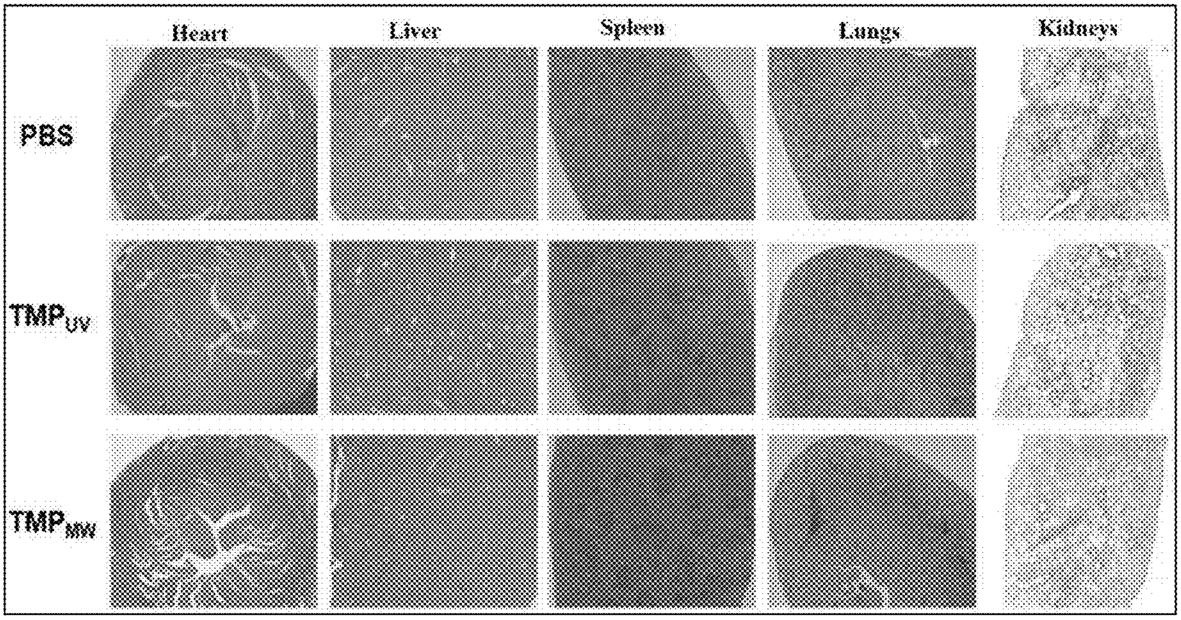
FIG. 15 is a schematic diagram of a hematoxylin-eosin (H&E) staining optical microscopy (4×) of important organs.

The biosafety of a new type of nanomaterial for treating diseases is an important aspect that must be verified in an application process. Only by ensuring the biosafety can future clinical transformation become possible. The indexes related to liver and kidney functions are tested, including an alanine transaminase (ALT), an aspartate transaminase (AST), total bilirubin (TBil) and serum creatinine (CRE), and the results showed that the $TMP_{MW}$ had no obvious hepatorenal toxicity (FIGS. 14A, 14B, 14C, and 14D). Then, important organs (a heart, a liver, a spleen, lungs, and kidneys) of the tumor model mice are further sampled after the intervention and performed a hematoxylin-eosin (H&E) staining. The results showed that the $TMP_{MW}$ had no significant damage to the important organs (FIG. 15).

Figure 16:
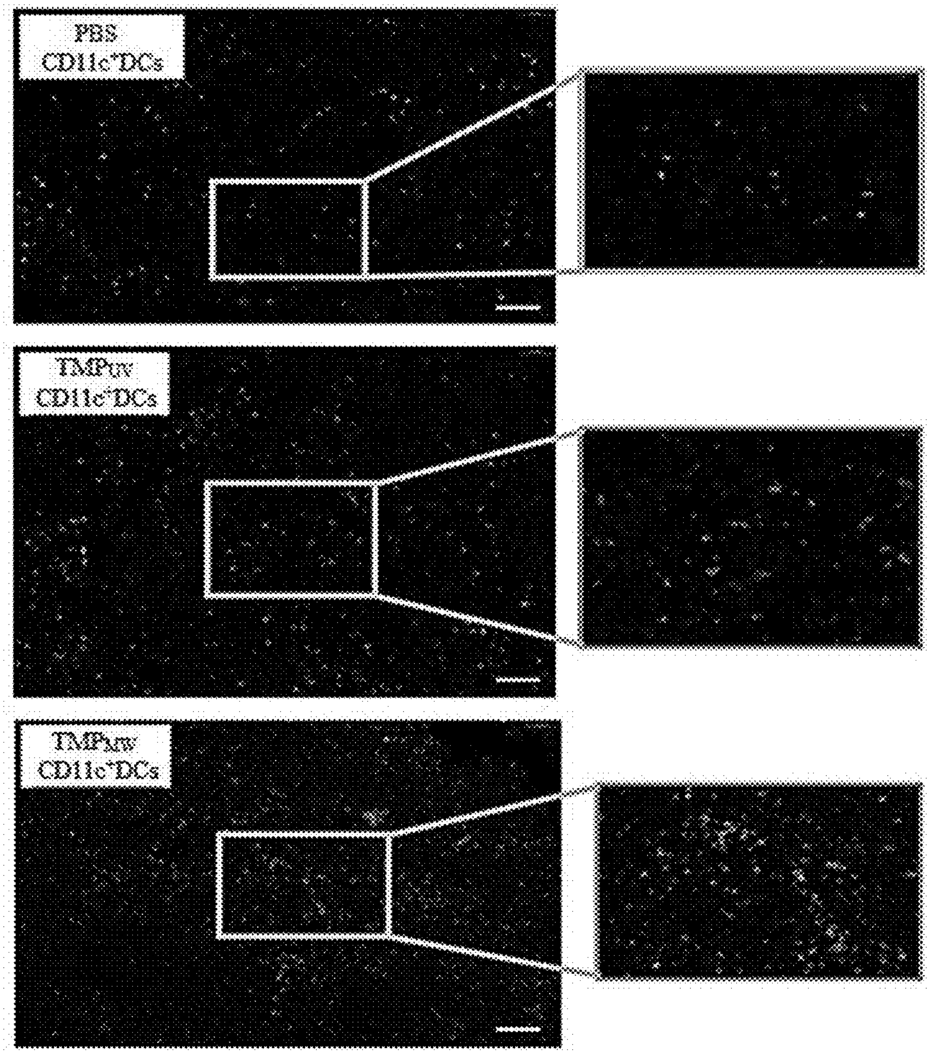
FIG. 16 is a schematic diagram of an immunofluorescence pattern of a dendritic cell (DCs) in a mouse tumor tissue.
Figure 17:
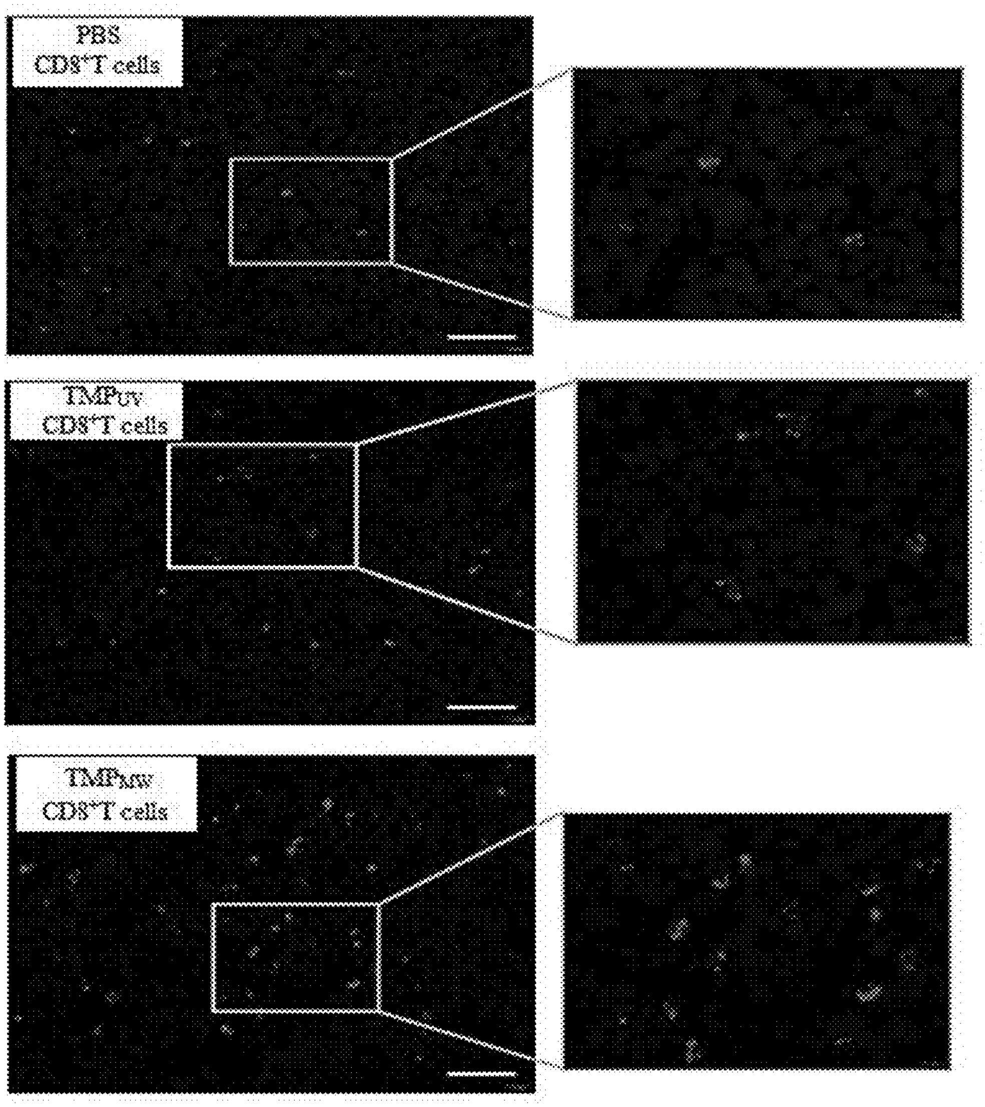
FIG. 17 is a schematic diagram of an immunofluorescence pattern of a $CD8^+$ T cell in the mouse tumor tissue.

6. The Effect of $TMP_{MW}$ on a Tumor Immune Microenvironment at the Animal Level At past, it is found that the TMPs encapsulating metabolic inhibitors reverse the tumor immune microenvironment. Therefore, in order to preliminarily explore a therapeutic mechanism of the $TMP_{MW}$, an immunofluorescence staining is performed on dendritic cells (DCs) and $CD8^+$ T cells in a mouse tumor tissue (FIGS. 16 and 17). The immunofluorescence staining shows that the $TMP_{MW}$ promotes an infiltration of the DCs with antigen presenting effect and the $CD8^+$ T cells with tumor cell killing effect, and the immunofluorescence staining indicates that the $TMP_{MW}$ has the potential to improve the tumor immune microenvironment and develop as a tumor vaccine.

Figure 18:
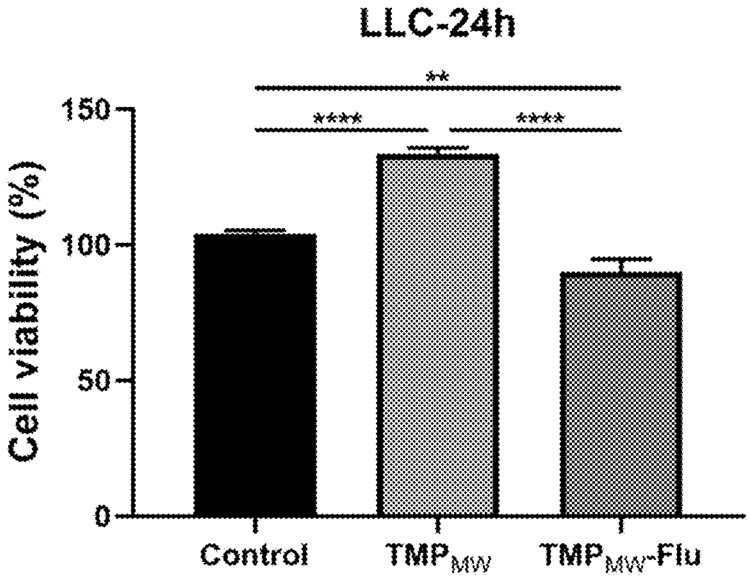
FIG. 18 is a schematic diagram of a result of a cell counting kit-8 (CCK8) experiment reflecting cell proliferation, $P<0.01$, and **$P<0.0001$.

7. An Exploration of the $TMP_{MW}$ as a Drug Delivery Platform for a Cancer Treatment 7.1 The $TMP_{MW}$ Encapsulating a Metabolic Inhibitor In addition to a single application of the empty $TMP_{MW}$ in a field of a tumor therapy, we continue to explore its potential for the drug delivery to enhance the tumor efficacy of the $TMP_{MW}$. Firstly, based on existing research, the metabolic inhibitor Fluvastatin (Flu) is co incubated with microwave induced tumor cell LLC, and after 24 h, the $TMP_{MW}$ ($TMP_{MW}$-Flu) containing Flu is extracted using the same gradient centrifugation step as before. At the cellular level, it is found that after 24 hours of the stimulation in the LLC, compared to the control group without the stimulation and the experimental group with only the $TMP_{MW}$, the $TMP_{MW}$-Flu shows a significant inhibitory effect on the cell proliferation (FIG. 18).

7.2 The $TMP_{MW}$ Encapsulating a Chemotherapy Drug

Figure 19:
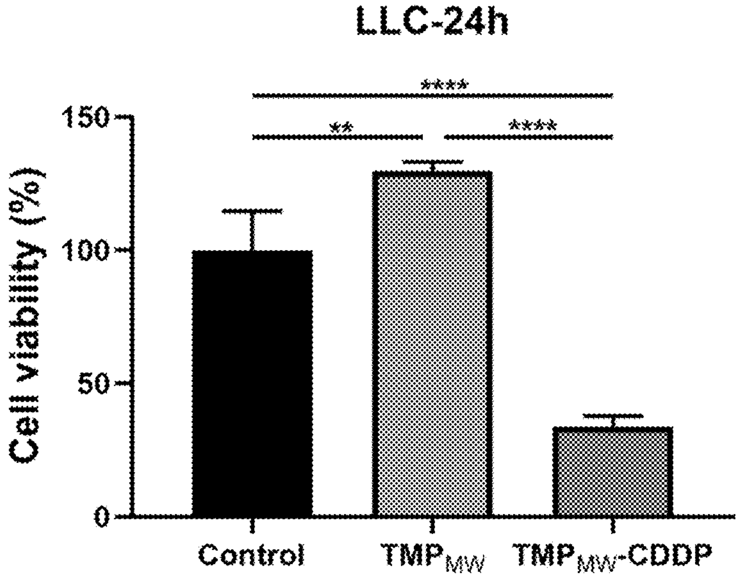
FIG. 19 is a schematic diagram of a result of a CCK8 experiment reflecting cell proliferation, $P<0.01$, and **$P<0.0001$.

A packaging capacity of the $TMP_{MW}$ is continued to explore. Based on a chemotherapy as a mandatory option for most cancer types, a possibility of successfully preparing the $TMP_{MW}$ containing the chemotherapy drug is explored. Regarding the chemotherapy drug, a traditional platinum-based chemotherapy drug—cisplatin (CDDP) is chosen. A drug encapsulating technology is the same as before. At the cellular level, after 24 h of the stimulation in the LLC, it is found that the $TMP_{MW}$ encapsulating CDDP ($TMP_{MW}$-CDDP) has a more significant inhibitory effect on the cell proliferation (FIG. 19).

The above are embodiments of the best embodiments in the disclosure, and the parts not detailed are common knowledge of those skilled in the art. A scope of the protection of the disclosure is subject to contents of claims, and any equivalent transformation based on the technical inspiration of the disclosure is further within the scope of the protection of the disclosure.

What is claimed is:

1. A method for preparing a tumor-derived microparticle by a microwave, comprising following steps:

step 1, taking Lewis lung carcinoma (LLC) of a lung adenocarcinoma cell line and then culturing the LCC in a culture dish for more than 24 hours (h) to obtain cultured cells;

step 2: performing a microwave heating treatment on the cultured cells obtained in step 1 with a microwave power of 350-700 watts (W) and a heating time of 10-20 seconds(s) to obtain treated cells;

step 3: placing the treated cells obtained in step 2 into a constant temperature incubator for cultivation of 24 h; and step 4: collecting a supernatant of cells from the culture dish cultured in step 3, and performing multiple centrifugation treatments on the supernatant by using a density gradient centrifugation method to obtain a precipitate which is the tumor-derived microparticle $TMP_{MW}$.

2. The method for preparing the tumor-derived microparticle by the microwave as claimed in claim 1, wherein in step 2, the microwave power is 700 W and the heating time is 20 s.

3. The method for preparing the tumor-derived microparticle by the microwave as claimed in claim 1, wherein in step 3, a culture temperature of the constant temperature incubator is 37° C. and a concentration of $CO_2$ is 5%.

4. The tumor-derived microparticle prepared by the method as claimed in claim 1.

* * * * *